(12) United States Patent
Hagen et al.

(10) Patent No.: US 10,409,275 B2
(45) Date of Patent: Sep. 10, 2019

(54) OIL DEBRIS MONITORING (ODM) WITH ADAPTIVE LEARNING

(71) Applicant: United Technologies Corporation, Farmington, CT (US)

(72) Inventors: Gregory S. Hagen, Glastonbury, CT (US); Yiqing Lin, Glastonbury, CT (US); Ozgur Erdinc, Coventry, CT (US); Michael J. Giering, Bolton, CT (US); Alexander I. Khibnik, Glastonbury, CT (US)

(73) Assignee: UNITED TECHNOLOGIES CORPORATION, Farmington, CT (US)

( * ) Notice: Subject to any disclaimer, the term of this patent is extended or adjusted under 35 U.S.C. 154(b) by 247 days.

(21) Appl. No.: 15/297,319

(22) Filed: Oct. 19, 2016

(65) Prior Publication Data

US 2018/0107203 A1 Apr. 19, 2018

(51) Int. Cl.
*G05B 23/02* (2006.01)
*F01D 21/00* (2006.01)
(Continued)

(52) U.S. Cl.
CPC ....... *G05B 23/0289* (2013.01); *F01D 21/003* (2013.01); *F01D 25/16* (2013.01);
(Continued)

(58) Field of Classification Search
None
See application file for complete search history.

(56) References Cited

U.S. PATENT DOCUMENTS

| 2005/0162119 A1* | 7/2005 | Landry | A47L 9/2805 318/580 |
| 2006/0064291 A1* | 3/2006 | Pattipatti | G05B 23/0243 703/14 |

(Continued)

FOREIGN PATENT DOCUMENTS

EP 2169221 A2 3/2010

OTHER PUBLICATIONS

Extended European Search Report; European Patent Application No. 17185925.8; European Filing Date: Aug. 18, 2017; dated Dec. 22, 2017; 10 pages.

(Continued)

*Primary Examiner* — Tuan C Dao
(74) *Attorney, Agent, or Firm* — Cantor Colburn LLP

(57) ABSTRACT

A system and method for debris particle detection with adaptive learning are provided. The method includes receiving oil debris monitoring (ODM) sensor data from an oil debris monitor sensor and fleet data from a database, detecting a feature in the ODM sensor data, generating an anomaly detection signal based on detecting an anomaly by comparing the feature in the ODM sensor data to a limit defined by system information stored in the fleet data, selecting a maintenance action request based on the anomaly detection signal, and adjusting one or more of the feature, the anomaly, the limit, and the maintenance action request by applying an adaptive learning algorithm that uses the ODM sensor data, fleet data, and feedback from field maintenance of one or more engines that evolves over time.

16 Claims, 7 Drawing Sheets

(51) Int. Cl.

| | | |
|---|---|---|
| *F01D 25/16* | (2006.01) | |
| *F01D 25/18* | (2006.01) | |
| *G01N 33/28* | (2006.01) | |
| *G05B 13/02* | (2006.01) | |
| *F16N 29/00* | (2006.01) | |
| *G06N 20/00* | (2019.01) | |
| *F16H 57/04* | (2010.01) | |

(52) U.S. Cl.
CPC ............ *F01D 25/18* (2013.01); *F16N 29/00* (2013.01); *G01N 33/2835* (2013.01); *G01N 33/2858* (2013.01); *G05B 13/0265* (2013.01); *G05B 23/0205* (2013.01); *F05D 2220/32* (2013.01); *F16H 57/0405* (2013.01); *G06N 20/00* (2019.01)

(56) References Cited

U.S. PATENT DOCUMENTS

| | | | | |
|---|---|---|---|---|
| 2007/0198215 | A1* | 8/2007 | Bonanni | G05B 23/0251 |
| | | | | 702/183 |
| 2008/0213445 | A1* | 9/2008 | Feinberg | A47J 37/1223 |
| | | | | 426/417 |
| 2010/0186390 | A1* | 7/2010 | Perry | F01N 3/2073 |
| | | | | 60/295 |
| 2011/0125419 | A1* | 5/2011 | Bechhoefer | F03D 7/047 |
| | | | | 702/34 |
| 2011/0224917 | A1* | 9/2011 | Uluyol | G01M 13/045 |
| | | | | 702/34 |
| 2013/0130573 | A1* | 5/2013 | Kuriyagawa | B63H 20/00 |
| | | | | 440/2 |
| 2017/0234113 | A1* | 8/2017 | Steele | E21B 34/10 |
| | | | | 166/381 |

OTHER PUBLICATIONS

I. Morgan et al., "Detection and Diagnosis of Incipient Faults in Heavy-Duty Diesel Engines", IEEE Transactions on Industrial Electronics, vol. 57, No. 10, Oct. 2010, pp. 3522-3532.

R. F. Orsagh et al., "Prognostics/Diagnostics for Gas Turbine Engine Bearings", 2003 IEEE, vol. 7-3095, pp. 1165-1173.

S-L A. Alcock et al., "The Development of an Advanced Diagnostic/Prognostic System for the RB199 Aero Engine", Aerospace Conference, 2005 IEEE, IEEE, Mar. 5, 2005, pp. 1-9.

* cited by examiner

OIL DEBRIS MONITORING (ODM) WITH ADAPTIVE LEARNING

STATEMENT OF FEDERAL SUPPORT

This invention was made with Government support under Contract No. N00019-02-C-3003 awarded by the Navy. The government therefore has certain rights in this invention.

BACKGROUND

The subject matter disclosed herein generally relates to oil debris monitoring and, more particularly, to oil debris monitoring in an engine.

Oil debris can be present in oil flowing through an engine system for a number of different reasons. For example, as engine components in an engine system wear, particulate will enter the oil that is lubricating the engine system. Specifically, the particulate can be generated from engine component breakdown, a breakdown of the oil itself, environmental conditions that introduce contaminating particulate that becomes the oil debris, and/or any combination thereof.

In order to determine the amount of oil debris in the oil, the oil can be configured to pass through an oil debris monitor that can approximate the amount of debris in the oil by monitoring different properties of the oil that passes through the oil debris monitor. However, the accuracy of the oil debris monitor is affected by many factors such as the flow volatility of the oil. For example, the flow of oil is controlled and affected by multiple valves distributed throughout the engine system as well as changes in component arrangement. Further, oil debris monitoring parameters can change over time due to general wear and tear as well as adjustments and updates to the engine system made during maintenance actions that may go unaccounted for.

Accordingly, there is a desire for improved accuracy of the oil debris monitoring.

BRIEF DESCRIPTION

According to one embodiment a method for debris particle detection with adaptive learning is provided. The method includes receiving oil debris monitoring (ODM) sensor data from an oil debris monitor sensor and fleet data from a database, detecting a feature in the ODM sensor data, generating an anomaly detection signal based on detecting an anomaly by comparing the feature in the ODM sensor data to a limit defined by system information stored in the fleet data, selecting a maintenance action based on the anomaly detection signal, and adjusting one or more of the feature, the anomaly, the limit, and the maintenance action request by applying an adaptive learning algorithm that uses the ODM sensor data, fleet data, and feedback from field maintenance of one or more engines that evolves over time.

In addition to one or more of the features described above, or as an alternative, further embodiments may include, where the adaptive learning algorithm is one selected from a group consisting of a machine learning algorithm, a supervised machine learning classification algorithm, and a support vector machine (SVM) algorithm.

In addition to one or more of the features described above, or as an alternative, further embodiments may include, where applying adaptive learning on ODM sensor data further includes training a first a set of historical sensor data from fleet data to differentiate the characteristics of parameters with or without a particle.

In addition to one or more of the features described above, or as an alternative, further embodiments may include applying the adaptive learning algorithm to on-board parameters to detect particles in real-time.

In addition to one or more of the features described above, or as an alternative, further embodiments may include collecting field maintenance data to serve as ground truth of particle detection.

In addition to one or more of the features described above, or as an alternative, further embodiments may include, where field maintenance data includes one or more of data indicating whether a real particle is detected, data indicating signal noise has been falsely identified as particles, and data indicating sensor fault.

In addition to one or more of the features described above, or as an alternative, further embodiments may include a fine-tuning procedure that includes finding a discrepancy between a detection algorithm that is used to detect the features in the ODM sensor data and fleet data, generating additional training data from the discrepancy, and adding the additional training data to a training set to fine-tune the adaptive learning algorithm.

In addition to one or more of the features described above, or as an alternative, further embodiments may include applying the fine-tuning procedure to data from at least one selected from a group including a single engine, a collection of engines in the fleet data, engines from a different fleet, and engines of customers.

In addition to one or more of the features described above, or as an alternative, further embodiments may include applying the fine-tuning procedure to each individual engine to reflect its unique characteristics.

In addition to one or more of the features described above, or as an alternative, further embodiments may include, where applying the adaptive learning algorithm continues until a detection algorithm produces detection accuracy that meets or exceeds a detection accuracy threshold.

In addition to one or more of the features described above, or as an alternative, further embodiments may include collecting field maintenance data from a subset of engine data obtained from a limited set stored in fleet data.

In addition to one or more of the features described above, or as an alternative, further embodiments may include adjusting the adaptive particle detection algorithm if additional ODM sensor parameters are included in fleet data at any time, and re-training adaptive particle detection algorithms.

In addition to one or more of the features described above, or as an alternative, further embodiments may include adjusting one or more of the feature, the anomaly, the limit, and the maintenance action request upon receiving feedback from field maintenance of one or more engines.

In addition to one or more of the features described above, or as an alternative, further embodiments may include enabling particle detection algorithms to learn from actual data from field maintenance, and adjusting a discrepancy learned from field maintenance.

According to another embodiment a system for debris particle detection with adaptive learning is provided. The system includes a memory having computer readable instructions, and a processor configured to execute the computer readable instructions. The computer readable instructions including receiving oil debris monitoring (ODM) sensor data from an oil debris monitor sensor and fleet data from a database, detecting a feature in the ODM sensor data, generating an anomaly detection signal based on detecting an anomaly by comparing the feature in the ODM sensor data to a limit defined by system information stored in the fleet data, selecting a maintenance action based on the anomaly detection signal, and adjusting one or more of the feature, the anomaly, the limit, and the maintenance action request by applying an adaptive learning algorithm that uses the ODM sensor data, fleet data, and feedback from field maintenance of one or more engines that evolves over time.

In addition to one or more of the features described above, or as an alternative, further embodiments may include, where the computer readable instructions further include training a first a set of historical sensor data from fleet data to differentiate the characteristics of parameters with or without a particle.

In addition to one or more of the features described above, or as an alternative, further embodiments may include, where the computer readable instructions further include applying the adaptive learning algorithm to on-board parameters to detect particles in real-time.

In addition to one or more of the features described above, or as an alternative, further embodiments may include, where the computer readable instructions further include collecting field maintenance data to serve as ground truth of particle detection.

In addition to one or more of the features described above, or as an alternative, further embodiments may include, where the computer readable instructions further include a fine-tuning procedure that includes finding a discrepancy between a detection algorithm that is used to detect the features in the ODM sensor data and fleet data, generating additional training data from the discrepancy, and adding the additional training data related to the discrepancy to a training set to fine-tune the adaptive learning algorithm.

According to another embodiment a computer program product for debris particle detection with adaptive learning is provided. The computer program product including a computer readable storage medium having program instructions embodied therewith, the program instructions executable by a processor to cause the processor to receive oil debris monitoring (ODM) sensor data from an oil debris monitor sensor and fleet data from a database, detect a feature in the ODM sensor data, generate an anomaly detection signal based on detecting an anomaly by comparing the feature in the ODM sensor data to a limit defined by system information stored in the fleet data, select a maintenance action based on the anomaly detection signal, and adjusting one or more of the feature, the anomaly, the limit, and the maintenance request by applying an adaptive learning algorithm that uses the ODM sensor data, fleet data, and feedback from field maintenance of one or more engines that evolves over time.

The foregoing features and elements may be combined in various combinations without exclusivity, unless expressly indicated otherwise. These features and elements as well as the operation thereof will become more apparent in light of the following description and the accompanying drawings. It should be understood, however, that the following description and drawings are intended to be illustrative and explanatory in nature and non-limiting.

BRIEF DESCRIPTION OF THE DRAWINGS

The foregoing and other features, and advantages of the present disclosure are apparent from the following detailed description taken in conjunction with the accompanying drawings in which.

DETAILED DESCRIPTION

Figure 1:
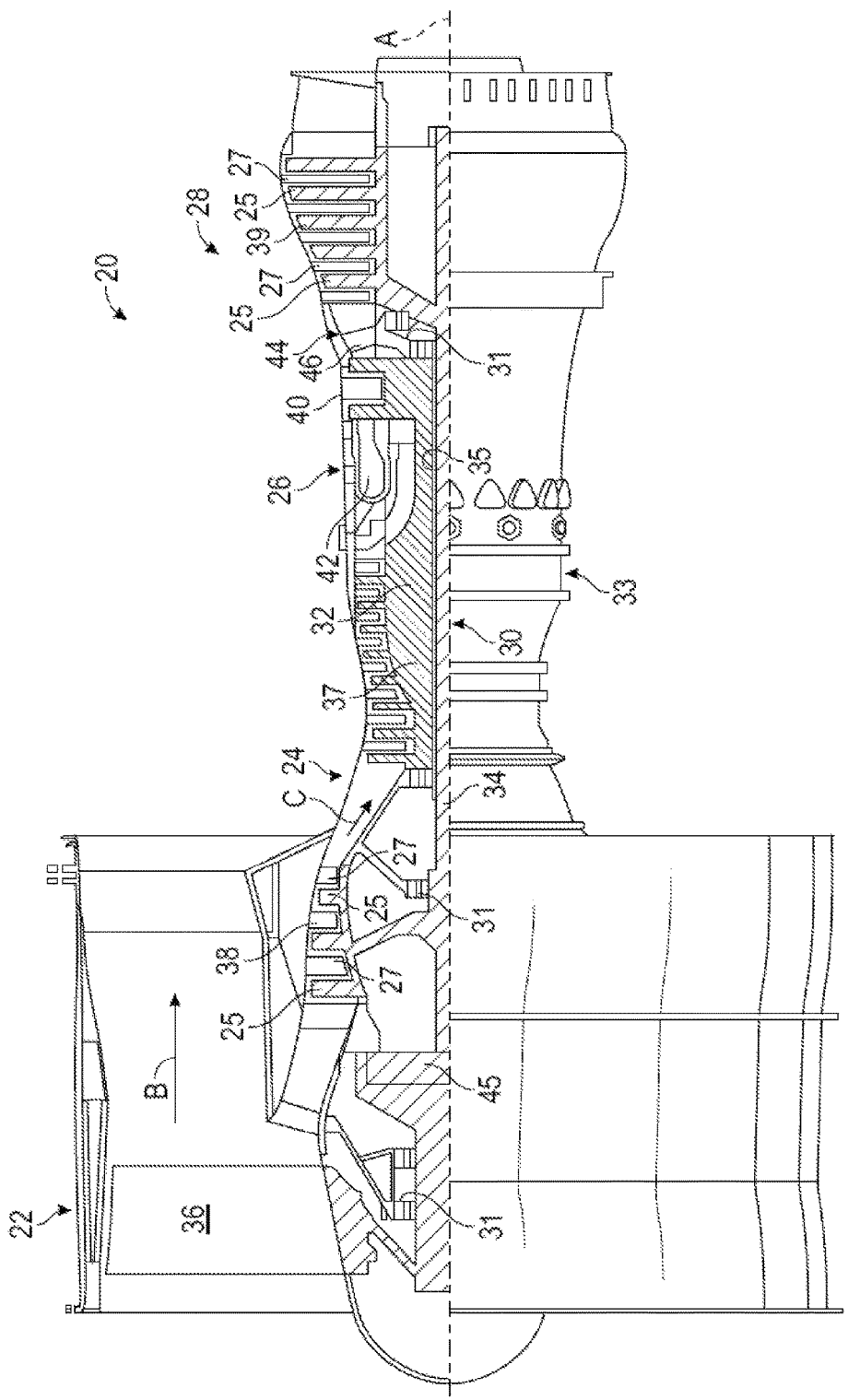
FIG. 1 is a schematic cross-sectional illustration of a gas turbine engine that may employ various embodiments disclosed herein.

As shown and described herein, various features of the disclosure will be presented. Various embodiments may have the same or similar features and thus the same or similar features may be labeled with the same reference numeral, but preceded by a different first number indicating the figure to which the feature is shown. Thus, for example, element "a" that is shown in FIG. X may be labeled "Xa" and a similar feature in FIG. Z may be labeled "Za." Although similar reference numbers may be used in a generic sense, various embodiments will be described and various features may include changes, alterations, modifications, etc. as will be appreciated by those of skill in the art, whether explicitly described or otherwise would be appreciated by those of skill in the art.

Embodiments described herein are directed to implementing a method and system for oil debris monitoring (ODM) with adaptive learning. The method and system uses system information to label collected signal features and detect anomalies in the system by comparing the signal features with system information. The labeling of collected signal features is done by using label definitions that each corresponds with a signal feature. Further, once an anomaly is detected, an anomaly detection signal is generated and a maintenance action to remedy the anomaly is selected and run based on the anomaly detection signal. The adaptive learning is included in the method and system and can update system information based on maintenance results. These updates further update the labeling and anomaly detection. The method can use an engine system that includes one or more apparatus such as a bypass valve and engine debris monitor and the method can include using such an apparatus for detecting particles in engine oil debris monitoring (ODM) system and adjusting properties based on limit comparisons.

For example, in accordance with one or more embodiments, an apparatus, and a method for using such an apparatus, for detecting particles in engine oil debris monitoring (ODM) system is provided. Engine lubricating oils are routinely monitored for the detection of possible particles, which may be early indications of component failure such as gearbox and bearing. Manual routine inspection can be complex and time-consuming. Thus, in accordance with one or more embodiments, monitoring is provided through condition-based maintenance which relies on sensor systems. There exist sensor systems aiming at automatically detecting particles in the lubricating system. However, robust particle detection can be a challenging task, as sensor signal characteristics may differ under various engine operating conditions and various noise levels. In addition, each engine may have its own ODM signal profiles due to its unique sensor and installation characteristics. According to an embodiment, detecting particles in a production environment are implemented using well-designed detection methods that can be adapted to various engines operating environment.

FIG. 1 schematically illustrates a gas turbine engine 20. The exemplary gas turbine engine 20 is a two-spool turbofan engine that generally incorporates a fan section 22, a compressor section 24, a combustor section 26, and a turbine section 28. Alternative engines might include an augmenter section (not shown) among other systems for features. The fan section 22 drives air along a bypass flow path B, while the compressor section 24 drives air along a core flow path C for compression and communication into the combustor section 26. Hot combustion gases generated in the combustor section 26 are expanded through the turbine section 28. Although depicted as a turbofan gas turbine engine in the disclosed non-limiting embodiment, it should be understood that the concepts described herein are not limited to turbofan engines and these teachings could extend to other types of engines, including but not limited to, three-spool engine architectures.

The gas turbine engine 20 generally includes a low speed spool 30 and a high speed spool 32 mounted for rotation about an engine centerline longitudinal axis A. The low speed spool 30 and the high speed spool 32 may be mounted relative to an engine static structure 33 via several bearing systems 31. It should be understood that other bearing systems 31 may alternatively or additionally be provided.

The low speed spool 30 generally includes an inner shaft 34 that interconnects a fan 36, a low pressure compressor 38 and a low pressure turbine 39. The inner shaft 34 can be connected to the fan 36 through a geared architecture 45 to drive the fan 36 at a lower speed than the low speed spool 30. The high speed spool 32 includes an outer shaft 35 that interconnects a high pressure compressor 37 and a high pressure turbine 40. In this embodiment, the inner shaft 34 and the outer shaft 35 are supported at various axial locations by bearing systems 31 positioned within the engine static structure 33.

A combustor 42 is arranged between the high pressure compressor 37 and the high pressure turbine 40. A mid-turbine frame 44 may be arranged generally between the high pressure turbine 40 and the low pressure turbine 39. The mid-turbine frame 44 can support one or more bearing systems 31 of the turbine section 28. The mid-turbine frame 44 may include one or more airfoils 46 that extend within the core flow path C.

The inner shaft 34 and the outer shaft 35 are concentric and rotate via the bearing systems 31 about the engine centerline longitudinal axis A, which is co-linear with their longitudinal axes. The core airflow is compressed by the low pressure compressor 38 and the high pressure compressor 37, is mixed with fuel and burned in the combustor 42, and is then expanded over the high pressure turbine 40 and the low pressure turbine 39. The high pressure turbine 40 and the low pressure turbine 39 rotationally drive the respective high speed spool 32 and the low speed spool 30 in response to the expansion.

Each of the compressor section 24 and the turbine section 28 may include alternating rows of rotor assemblies and vane assemblies (shown schematically) that carry airfoils that extend into the core flow path C. For example, the rotor assemblies can carry a plurality of rotating blades 25, while each vane assembly can carry a plurality of vanes 27 that extend into the core flow path C. The blades 25 of the rotor assemblies create or extract energy (in the form of pressure) from the core airflow that is communicated through the gas turbine engine 20 along the core flow path C. The vanes 27 of the vane assemblies direct the core airflow to the blades 25 to either add or extract energy.

Further, one or more of the engine components as shown have oil that flows in and/or around the components that is used to lubricate the components' movements as well as provide heat dissipation to help control engine component temperatures. The oil can be provided to the engine by an oil pump and valve system that also includes an oil flow controller. Additionally one or more sensors, such as an oil debris monitor, can be included to collect information about the oil that can indicate both the condition of the oil and also the condition of different components of the engine.

One or more embodiments of the present disclosure features an apparatus and/or associated method for optimizing mechanical system failure debris detection that utilizes system information that includes knowledge of the system's configuration settings to optimize signal processing algorithms to produce more accurate debris detection features. One or more embodiments include an oil debris monitor sensor. According to other embodiments system information includes the system's configuration settings that include, for example, state indicators of various valve settings, lubrication fluid temperatures, and pressures.

Figure 2:
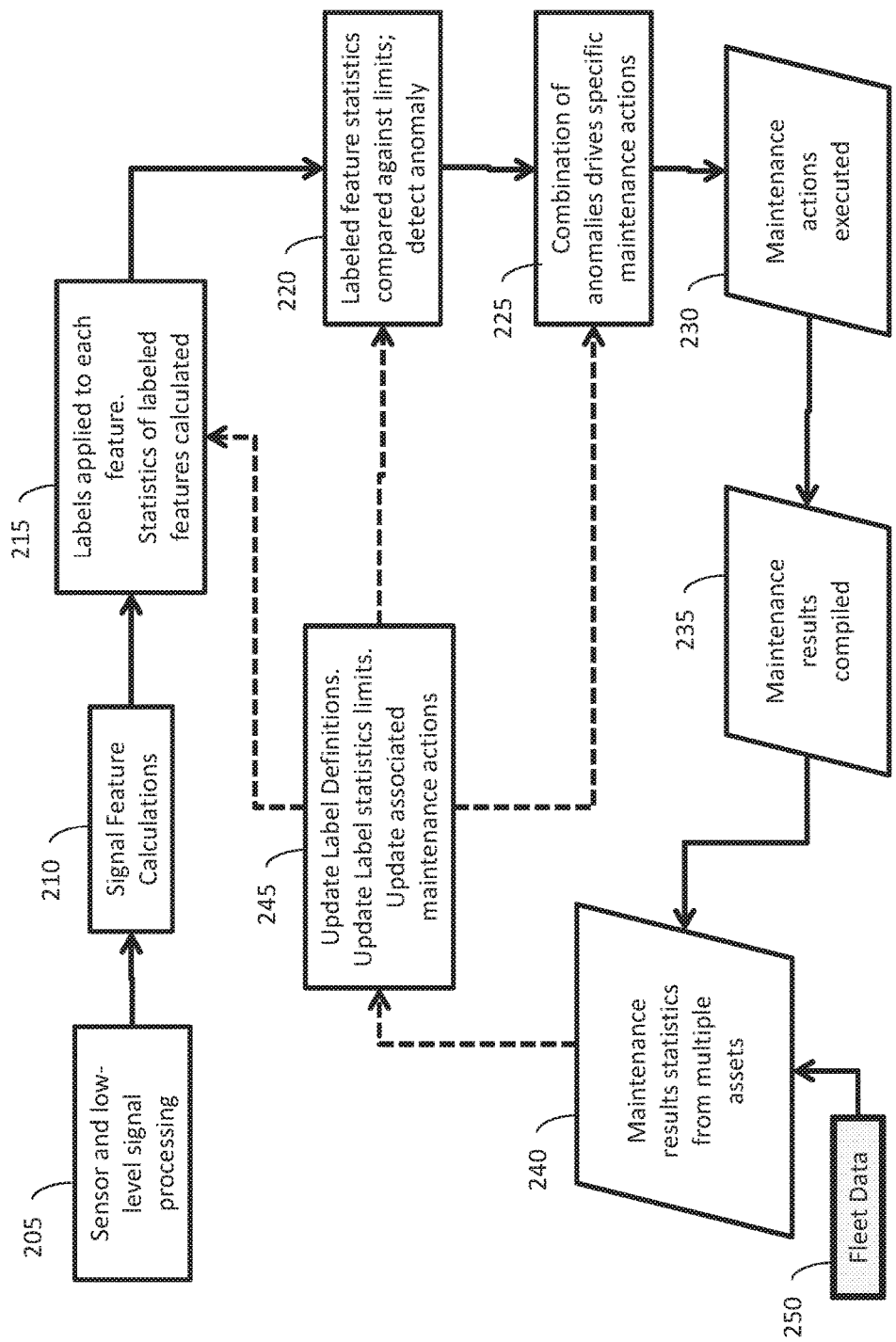
FIG. 2 is a block diagram of a method for feature detection and maintenance action selection using adaptive learning in accordance with one or more embodiments.

Turning now to FIG. 2, a block diagram of a method for feature detection and maintenance action selection using adaptive learning in accordance with one or more embodiments is shown. As shown, the method includes sensor and low-level signal processing (operation 205). This can include collecting sensor signals using, for example, an oil debris monitor sensor. The method then calculates signal features (operation 210). This can include processing the collected sensor signals into features. For example, the sensor signal can be processed and a feature of a magnetic value of the oil passing by the oil debris monitor sensor can be calculated from the signal. This signal signature can be processed to calculate other features such as the amount and type of metallic debris in the oil. The method then applies feature labels to each feature and calculates statistics of the labeled features (operation 215). These feature labels are defined by label definitions that correspond to particular features. For example, a label definition may be a particular magnetic value of oil. Thus, when that feature is detected in oil passing the oil debris monitor sensor it can be matched with the corresponding label definition. The corresponding feature label associated with that label definition can then be applied to that feature data.

The labeled feature statistics are then compared against limits based on system information to detect an anomaly (operation 220). An anomaly includes the system operating outside normal operating conditions and is defined by limits based on system information. For example, the system can have a particular temperature it operates at under normal conditions and therefore a limit can be set based on the system configuration or operational information. An anomaly would be detected if the labeled feature exceeds the limit.

Further the method drives specific maintenance actions. This is done with a combination of anomalies that drives the specific maintenance action requests (operation 225). For example, a feature can be detected that indicates particular metal debris is in the oil and another feature can also be detected that indicates that the amount of the debris is above a limit. Based on these anomalies a maintenance action of, for example, replacing an oil filter can be selected.

The system then runs the maintenance action (operation 230) and compiles results from the maintenance action (operation 235). The results can be stored in fleet data (250) which includes other system information and additional overall fleet information for other systems. Maintenance results are then processed to generate statistics from multiple assets such as the maintenance results that were compiled and other data provided in the fleet data 250 (operation 240). The maintenance results statistics are then used to update label definitions as well as label statistic limits used to detect anomalies (operation 245).

Further, the maintenance results statistics can be used to update associated maintenance action requests (operation 245). For example, the maintenance results statistics may indicate that changing the oil filter will not remedy the metallic debris content and therefore an update to the associated maintenance action request can be made to change the associated action to replacing parts made from the identified metallic content detected in the oil. Also, it may be found that in the fleet data the debris rate or accumulation limit should be lowered to provide additional longevity to the overall system thereby adjusting a label statistical anomaly limit. Further, features and their feature labels can also be adjusted, for example, it may be found that previous signature detection is more indicative of other metallic debris and therefore the feature label can be updated accordingly to show this adjustment.

Figure 3:
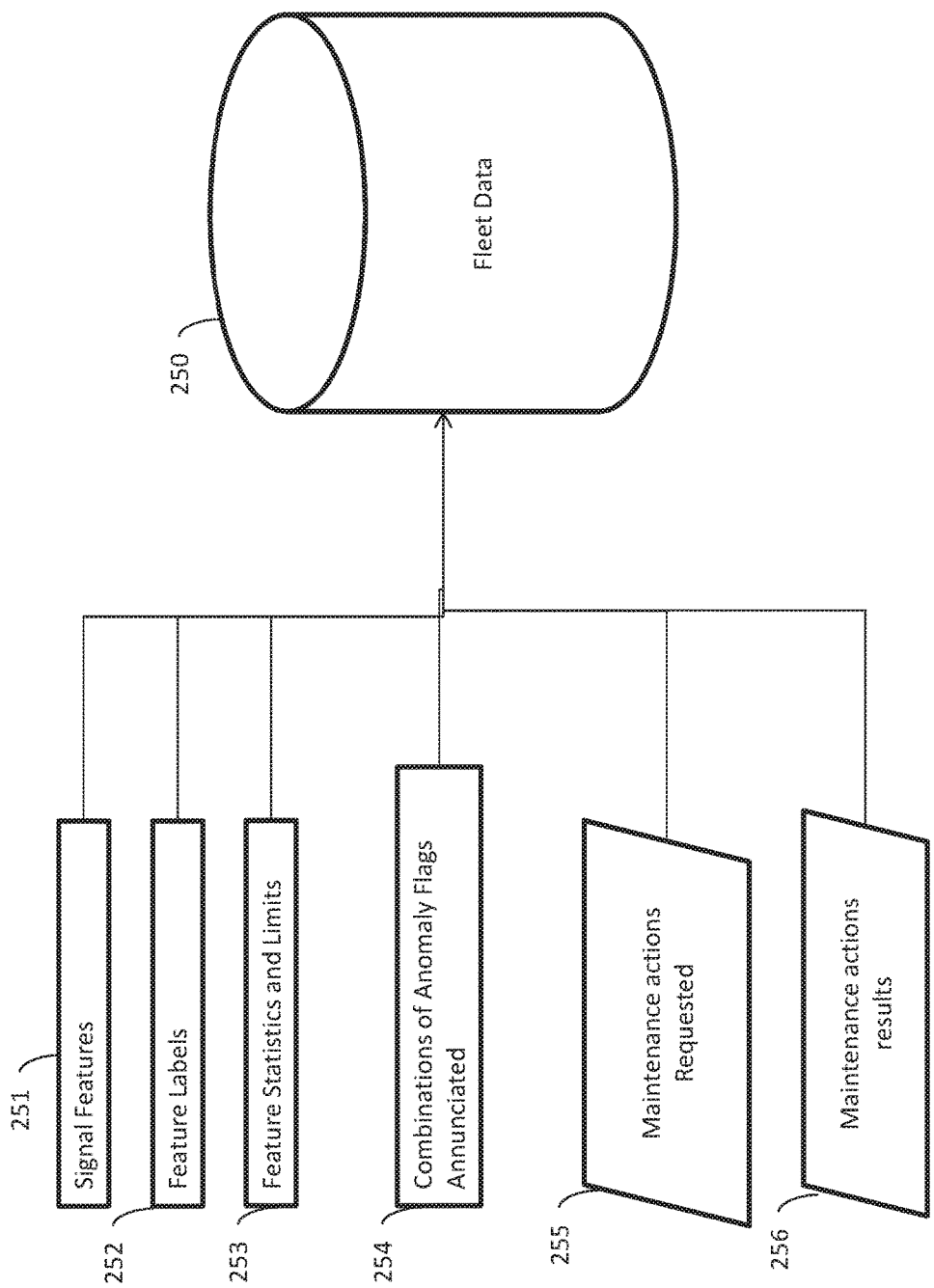
FIG. 3 is a block diagram of fleet data and the data that makes up fleet data in accordance with one or more embodiments.

FIG. 3 is a block diagram of fleet data and the data that makes up fleet data 250 in accordance with one or more embodiments. The fleet data 250 can contain information relating to any system, sub-system, analytics, statistics, other device, apparatus, or method generating content from anywhere in the fleet. The fleet includes fleet wide information, such as a number of aircrafts and aircraft components, that associated data is collected from and/or processed or generated data content derived thereof. For example, in accordance with one or more embodiments, the fleet data 250 includes signal features 251, feature labels 252, feature statistics and limits 253, combinations of anomaly flags annunciated 254, maintenance actions requested 255, and maintenance actions results 256. According to one or more embodiments, the fleet data is stored in a database. The database can be provided on a local storage device, a local server, a remote server, a distributed server system, and/or a combination thereof.

Figure 4:
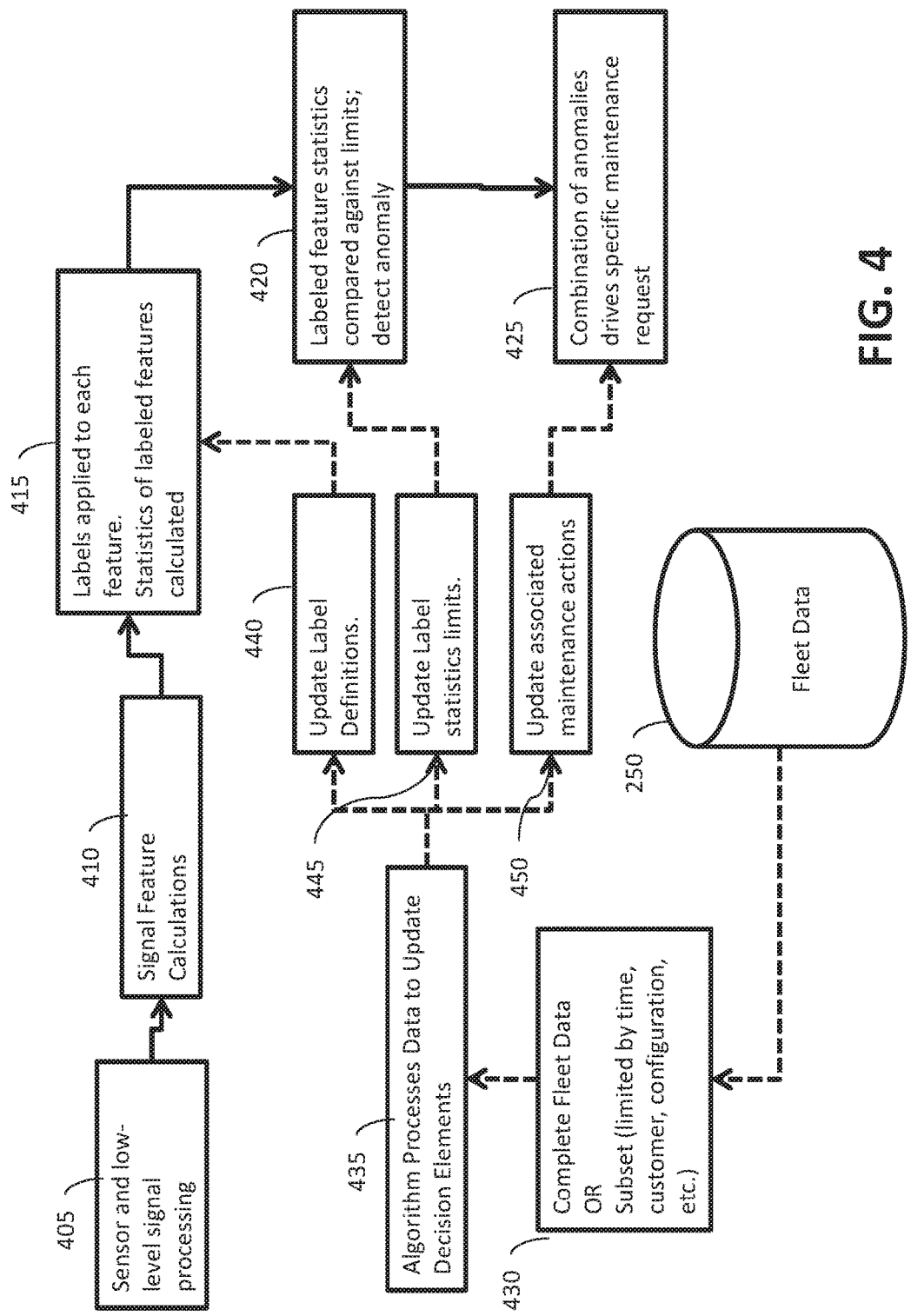
FIG. 4 is a block diagram of a method for feature detection and maintenance action selection using adaptive learning in accordance with one or more embodiments.

FIG. 4 is a block diagram of a method for feature detection and requested maintenance action selection using adaptive learning in accordance with one or more embodiments. The method includes sensor and low-level signal processing (operation 405). An example of which is collecting signals from an oil debris monitor and processing the signal to reduce signal noise signatures. The method also includes signal feature calculations (operation 410). For example the collected signal can be processed to calculate a signal value at a particular frequency known to contain the indicative information. Features can include configuration and/or operational states of the system being monitored. Further, the method includes feature labels being applied to each feature (operation 415). For example, a feature label such as the name of a metal can be applied to a sensor signal of a particular frequency value. Statistics of labeled features can be calculated as well (operation 415). The method also includes comparing labeled features statistics against limits and detecting one of more anomalies (operation 420). The method also includes combining anomalies to drive a specific maintenance request (operation 425).

As further shown the method includes using fleet data 250 to further process and update elements. Specifically, all of the fleet data or a subset of the data can be selected (operation 430). The subset of fleet data 250 can be limited by time, customer, configuration, etc. Further, algorithms for processing data can be included and used to update decision elements (operation 435). Particularly, label definitions can be updated (operation 440). Also, label statistical anomaly limits are updated (operation 445) and associated maintenance action requests are updated (operation 450).

In accordance with one or more embodiments, a debris particle detection method utilizes ODM sensor parameters as input. Further, the one or more embodiments of a debris particle detection method further includes applying adaptive learning algorithms that are capable of adjusting output and evolving over time based on feedback from field maintenance of multiple engines.

One example of the adaptive learning algorithms is a support vector machine (SVM), which is a supervised machine learning classification algorithm. According to an embodiment, to apply SVM on ODM sensor data, at first a set of historical sensor data from fleet data are used to train an algorithm to differentiate the characteristics of parameters with or without a particle. The trained algorithm is then applied to the on-board streaming parameters to detect particles in real-time. On-board streaming parameters are parameters that are collected on-board the ODM sensor circuit. According to an embodiment, field maintenance data can be collected to serve as a base for comparison used during particle detection. Field data can include whether a real particle is detected, whether noise has been falsely identified as particles, or the data indicates a sensor fault. If any discrepancy between detection algorithm and field data is found, additional training data generated from those discrepancy will be added to the training set to fine-tune the algorithm. This fine-tuning procedure may be applied to an engine fleet to capture the overall parameter characteristics or to each individual engine to reflect its unique characteristics. The adaptive learning can continue until the detection algorithm produces satisfactory detection accuracy. Then field maintenance data can be collected less frequently while still achieving satisfactory condition-based maintenance.

Furthermore, in accordance with one or more embodiments, if additional ODM sensor parameters are included in fleet data 250 at any time, the adaptive particle detection algorithms can be adjusted and re-trained to accommodate the new parameters without significant effort to re-design algorithms.

The proposed adaptive learning approach sets up a framework for continuous improvement of the accuracy of the detection algorithms that respond quickly to any feedback from field maintenance.

Further, one or more embodiments also enables particle detection algorithms to learn from actual data from field maintenance, and to quickly adjust to the discrepancy learned from field maintenance. This increases the success rate of detecting true events, and greatly improves false alarm rate.

Figure 5:
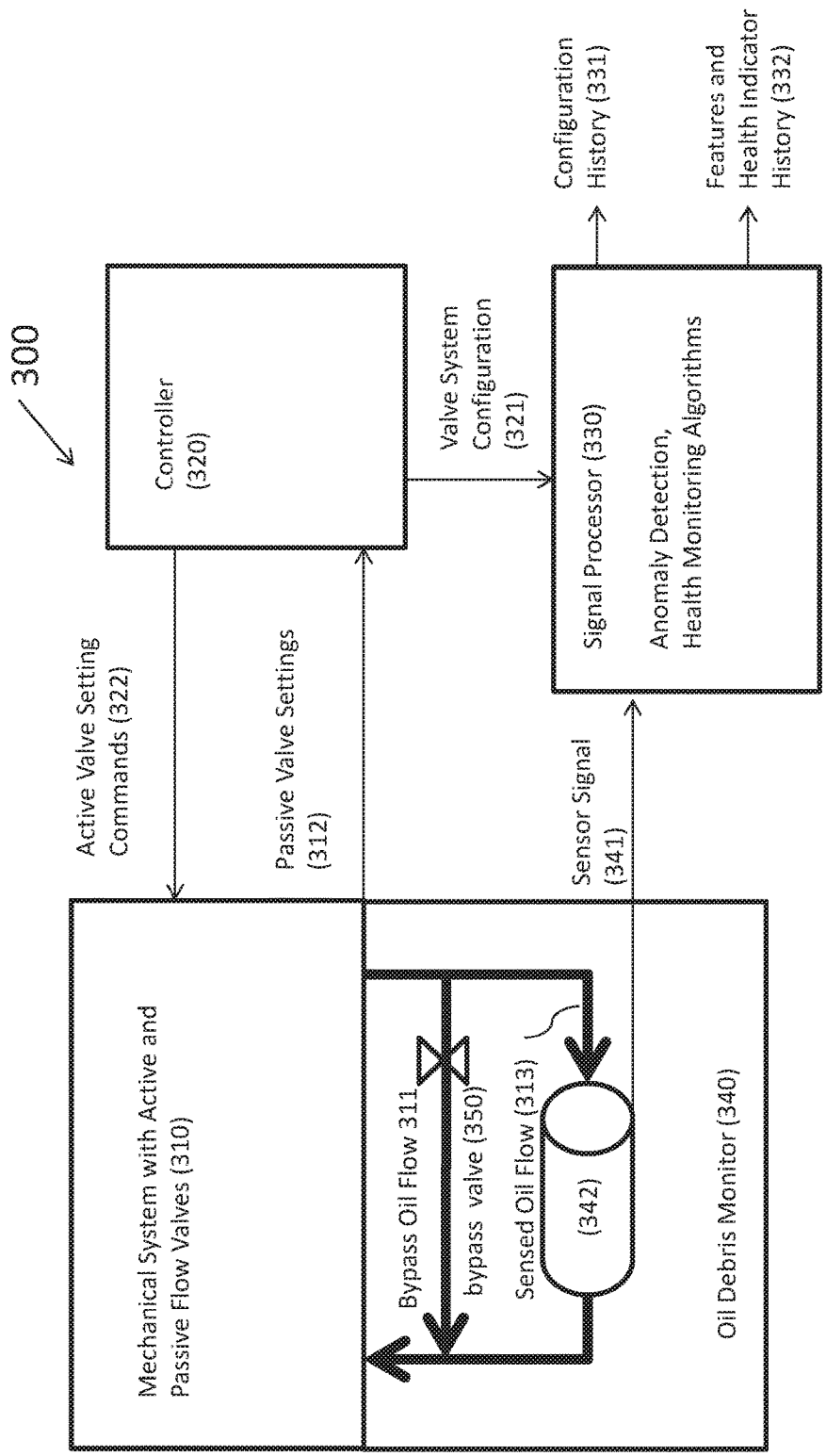
FIG. 5 is a block diagram of an engine system that includes an oil debris monitor and a bypass valve in accordance with one or more embodiments.

According to other embodiments, FIG. 5 depicts is a block diagram of an engine system 300 that includes at least an oil debris monitor 340 and a bypass valve 350 that can be used to implement the adaptive learning in accordance with one or more embodiments of the present disclosure.

Specifically, the gas turbine engine system 300 includes a mechanical system 310, such as the components shown in FIG. 1 of the gas turbine engine. The mechanical system 310 includes active and passive flow valves. The system 300 also includes an oil debris monitor 340 that includes an oil flow sensor 342 through which a particular sensed oil flow 313 passes. Further, the system 300 includes a controller 320 and a signal processor 330.

The controller 320 generates and provides commands to the mechanical system 310 and configuration information to the signal processor 330. For example, the controller 320 can specifically provide active valve setting commands 322 to the mechanical system 310. The mechanical system 310 can in turn provide passive valve settings 312 back to the controller 320. Additionally, the oil debris monitor 340 can provide a sensor signal 341 to the signal processor 330. The signal processor 330 can provide anomaly detection using the received sensor signal 341 and one or more health monitoring algorithms contained therewith. Further, the signal processor 330 can also provide configuration history 331. Additionally, the signal processor 330 can process the received sensor signal 341 and any other signals that are received to detect features and health indicator of different components based on what is detected in the sensed oil flow 313 through the oil debris monitor 340. The signal processor 330 is an example of a processor configured to execute the computer readable instructions that can be stored in memory located internal or external to the signal processor 330.

In accordance with one or more embodiments, the bypass valve 350 can be adjusted such that a consistent sensed oil flow 313 can be provided to the oil debris monitor 340. Specifically, the consistent sensed oil flow 313 can be provided by adjusting the bypass oil flow 311 to compensate for any changes in the oil flow caused by the mechanical system 310 with active and passive valves. The sensor signal 341 can be processed by the signal processor 330 for system features and health indicator values that are more accurate since the sensed oil flow 313 is known and consistent.

For example, the specific type and amount of particulate can be detected in the oil that is flowing by at a particular consistent rate during one or more modes of operation. This material can sometimes be identified as originating from a specific element/device in the engine system. Further, the existence of such quantities can indicate a particular wear condition of the component.

Figure 6:
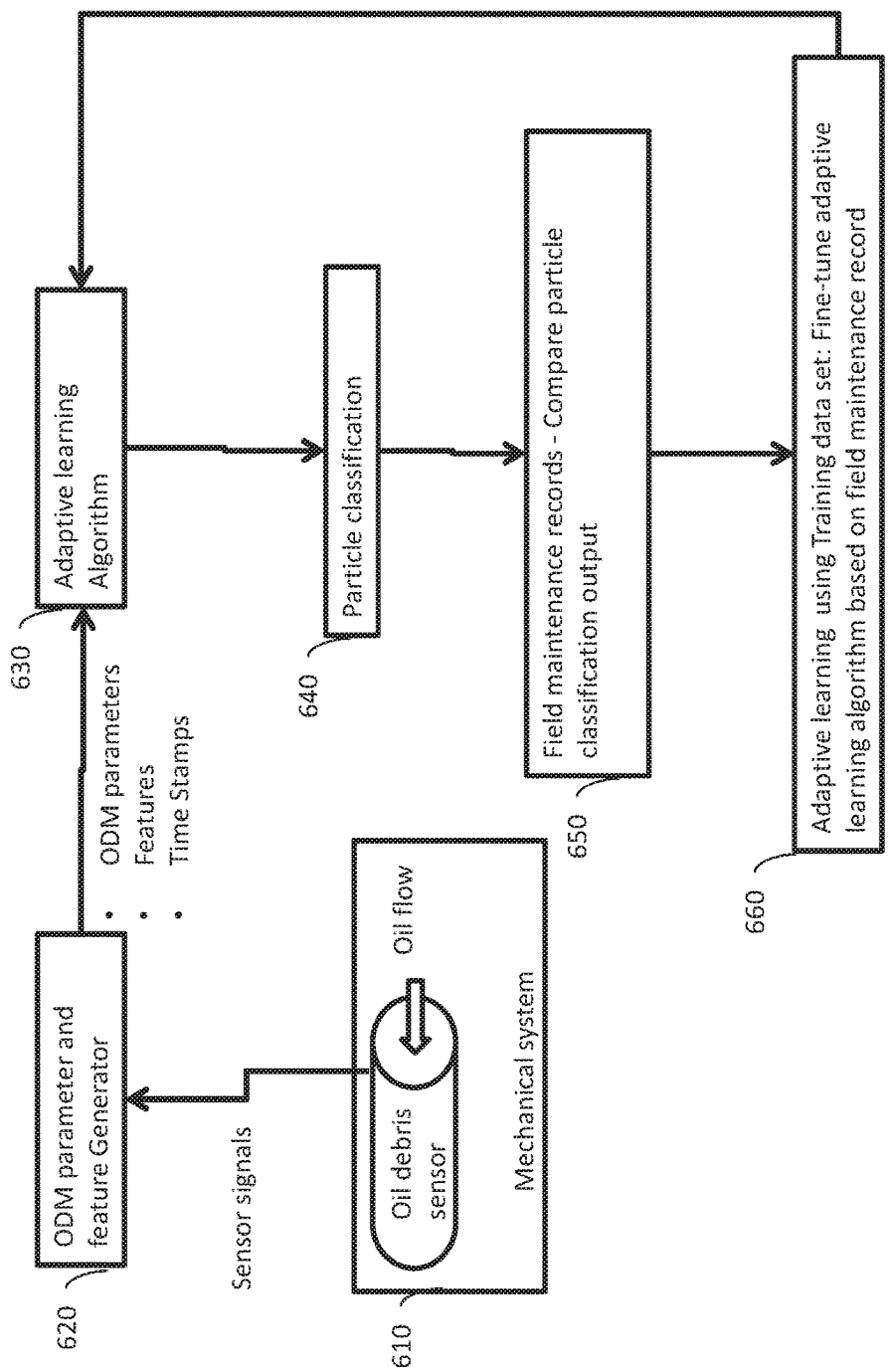
FIG. 6 is a block diagram of a method for feature detection and maintenance action selection using adaptive learning in accordance with one or more embodiments.

FIG. 6 is a block diagram of a specific flow diagram of a method and system for feature detection and maintenance action selection using adaptive learning in accordance with one or more embodiments. As show, a mechanical system includes an oil debris sensor through which oil flows (610). The mechanical system can include gears, bearings, seals, valves, etc. One or more sensor signal collected by the oil debris sensor includes raw high speed data.

The sensor signals collected from the oil debris sensor are transmitted to an ODM parameter and feature generator (620). This generator has a signal detector that detects the received sensor signal and processes the signal into a form that allows the generator to calculate parameters and generalized features. The ODM parameters, features, and time stamp values are transmitted from the generator to an adaptive learning algorithm implementing module (630). This adaptive learning portion applies one or more trained adaptive learning algorithm to classify particle versus non-particle signals. An example of a trained adaptive learning algorithm includes a support vector machine.

A particle classification (640) is output from the adaptive learning algorithm application (630). The particle classification 640 is done using an algorithm that classifies sensor signals as particles and non-particles based on given parameters and features After classification of the sensor signal is done, the particle classification output is compared to a field maintenance record (650). This comparison can act as a ground truth of particle versus non-particle classification. Data with a classification discrepancy will be added to off-board training data set. The classification discrepancy can be between field records and the adaptive learning algorithm particle classification output.

Further, adaptive learning is provided in the form of fine-tuning of the adaptive learning algorithm based on at least the field maintenance record is also provided (660). According to an embodiment, a training data set uses historical ODM parameters and features with known particle/non-particle classifications to train an adaptive learning algorithm.

Figure 7:
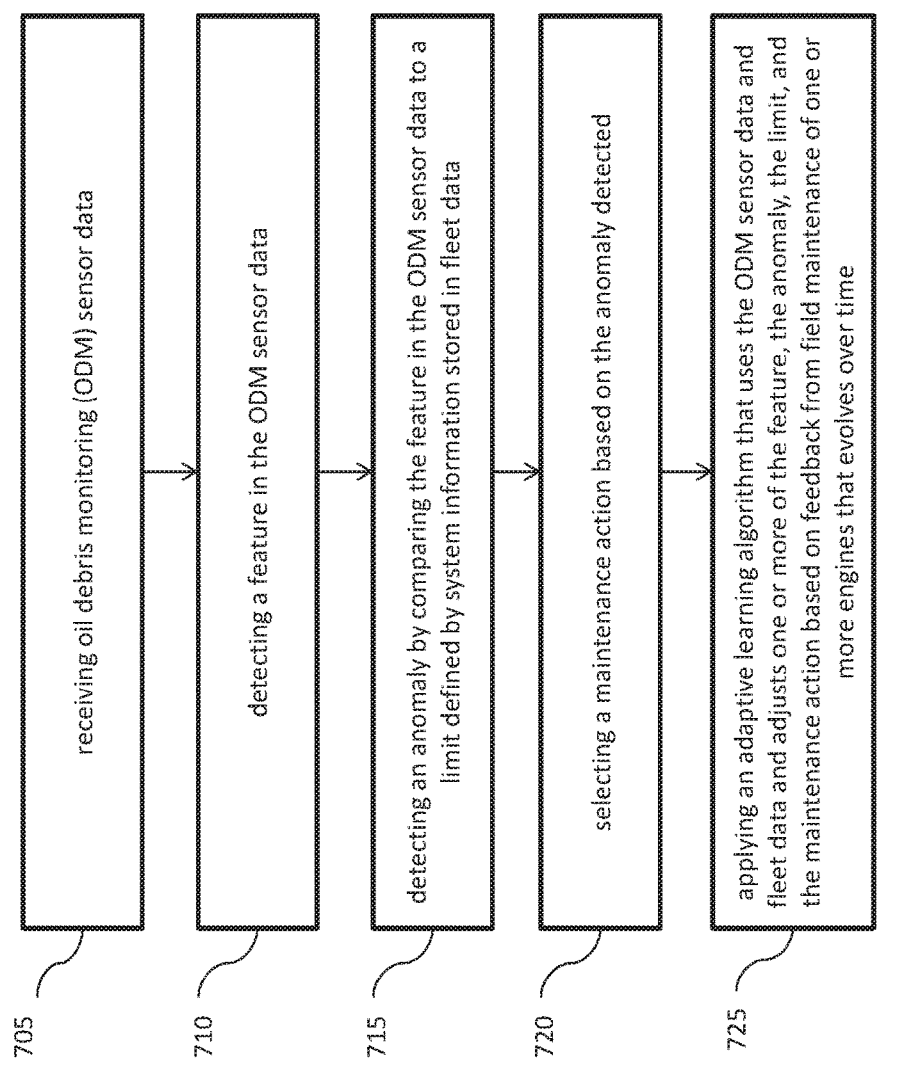
FIG. 7 is a flowchart of a method for monitoring oil debris in accordance with one or more embodiments.

FIG. 7 is a flowchart of a method 700 for monitoring oil debris in accordance with one or more embodiments of the present disclosure. The method 700 includes receiving oil debris monitoring (ODM) sensor data (operation 705). The method 700 further includes detecting a feature in the ODM sensor data (operation 710). Further, the method 700 includes detecting an anomaly by comparing the feature in the ODM sensor data to a limit defined by system information stored in fleet data (operation 715). The method further includes selecting a maintenance action request based on an anomaly detection signal indicating the anomaly detected (operation 720). The method also includes applying an adaptive learning algorithm that uses the ODM sensor data and fleet data and adjusts one or more of the feature, the anomaly, the limit, and the maintenance action request based on feedback from field maintenance of one or more engines that evolves over time (operation 725).

Further, according to one or more embodiments, an apparatus and associated method for optimizing mechanical system failure debris detection based on knowledge and data related to the machine, which in turn dictates which components are actively loaded and have a higher likelihood of exhibiting failure symptoms. The apparatus features a lube system with both actively and passively controlled valves. Actively controlled valves are driven by the system controls in order to provide lubrication system performance to meet the needs of the machine's current state of operation. Passively controlled valves, such as pressure-driven bypass valves, respond directly to the oil systems mechanical properties. The configuration state of the system is determined by the control system, either through direct commands for active valves or oil pressure and temperature measurements for passive valves. The control system uses this information to optimize signal processing algorithms (e.g., tuning based on time scales, frequencies, lubrication properties such as temperature and pressure) to more accurately detect signal features associated with mechanical system failure debris and to more effectively calculate health indicators that are customized to the specific failure modes associate with the components that are more heavily loaded and therefore more likely to fail.

In accordance with one or more embodiments, potential applications include, but are not limited to, the following examples:

In a vertical lift propulsion system, a lift fan mechanical system is engaged during powered lift. These configurations exhibit different flow rates through the oil debris monitor and result in different mechanical loadings on components in the system. Health indicators can be specifically defined for the different failure modes associated with each mode of operation. Furthermore, oil temperatures change during the different modes of operation. Accordingly, having a bypass valve can provide the control needed to stabilize the flow through the debris sensor.

Specifically, in one or more embodiments, an actively controlled bypass valve can be utilized to maintain a constant flow rate through the oil debris monitor. This allows the signal processing to be optimized for a more narrow range of flow rates.

In one or more embodiments, oil filter bypass valves may open when the filter gets clogged. This exposes the components to a higher risk of failure and may result in higher oil temperatures.

In one or more embodiments, thermal management systems may exhibit switching behavior that modifies the oil flow rates and temperatures throughout the system.

In accordance with one or more embodiments, at least one embodiment allows the signal processing to be more accurate by allowing a very narrow range of signal wavelengths to indicate debris.

Further, one or more embodiments allow the health indicators to be more accurately by specifically identifying which components are loaded during different modes of operation and assigning thresholds to produce failure detection capability more closely aligned with safety and reliability requirements.

In accordance with one or more embodiments, the adaptive learning algorithm is one selected from a group consisting of a machine learning algorithm, a support vector machine (SVM) algorithm, and a supervised machine learning classification algorithm. In accordance with one or more embodiments, applying adaptive learning on ODM sensor data further includes training a first a set of historical sensor data from fleet data to differentiate the characteristics of parameters with or without a particle. In accordance with one or more embodiments, the method also includes applying the adaptive learning algorithm to on-board parameters to detect particles in real-time. In accordance with one or more embodiments, the method also includes collecting field maintenance data to serve as ground truth of particle detection.

In accordance with one or more embodiments, field maintenance data includes one or more of data indicating whether a real particle is detected, data indicating signal noise has been falsely identified as particles, and data indicating sensor fault. In accordance with one or more embodiments, the method further includes a fine-tuning procedure that includes finding a discrepancy between a detection algorithm that is used to detect the features in the ODM sensor data and fleet data, generating additional training data from the discrepancy, and adding the additional training data to a training set to fine-tune the adaptive learning algorithm. In accordance with one or more embodiments, the method also includes applying the fine-tuning procedure to data from at least one selected from a group including a single engine, a collection of engines in the fleet data, engines from a different fleet, or engines of customers.

In accordance with one or more embodiments, the method also includes applying the fine-tuning procedure to each individual engine to reflect its unique characteristics. In accordance with one or more embodiments, applying the adaptive learning algorithm continues until a detection algorithm produces detection accuracy that meets or exceeds a detection accuracy threshold. In accordance with one or more embodiments, the method also includes collecting field maintenance data from a subset of engine data obtained from a limited set stored in fleet data.

In accordance with one or more embodiments, the method also includes adjusting the adaptive particle detection algorithm if additional ODM sensor parameters are included in fleet data at any time, and re-training adaptive particle detection algorithms to accommodate new parameters without significant effort to re-design algorithms. In accordance with one or more embodiments, the method further includes adjusting one or more of the feature, the anomaly, the limit, and the maintenance action request upon receiving feedback from field maintenance of one or more engines. In accordance with one or more embodiments, the method also includes enabling particle detection algorithms to learn from actual data from field maintenance, and adjusting a discrepancy learned from field maintenance.

While the present disclosure has been described in detail in connection with only a limited number of embodiments, it should be readily understood that the present disclosure is not limited to such disclosed embodiments. Rather, the present disclosure can be modified to incorporate any number of variations, alterations, substitutions, combinations, sub-combinations, or equivalent arrangements not heretofore described, but which are commensurate with the scope of the present disclosure. Additionally, while various embodiments of the present disclosure have been described, it is to be understood that aspects of the present disclosure may include only some of the described embodiments.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description has been presented for purposes of illustration and description, but is not intended to be exhaustive or limited to the embodiments in the form disclosed. Many modifications and variations will be apparent to those of ordinary skill in the art without departing from the scope of the disclosure. The embodiments were chosen and described in order to best explain the principles of the disclosure and the practical application, and to enable others of ordinary skill in the art to understand various embodiments with various modifications as are suited to the particular use contemplated.

The present embodiments may be a system, a method, and/or a computer program product at any possible technical detail level of integration. The computer program product may include a computer readable storage medium (or media) having computer readable program instructions thereon for causing a processor to carry out aspects of the present disclosure.

Aspects of the present invention are described herein with reference to flowchart illustrations and/or block diagrams of methods, apparatus (systems), and computer program products according to embodiments. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The flowchart and block diagrams in the Figures illustrate the architecture, functionality, and operation of possible implementations of systems, methods, and computer program products according to various embodiments. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Accordingly, the present disclosure is not to be seen as limited by the foregoing description, but is only limited by the scope of the appended claims.

What is claimed is:

1. A method for debris particle detection with adaptive learning in a gas turbine engine, the method comprising:
   delivering oil through a mechanical system including at least one of an active flow valve and a passive flow valve;
   sensing a flow of the oil using an oil debris monitor sensor;
   receiving, at a signal processor, oil debris monitoring (ODM) sensor data from the oil debris monitor sensor based on the sensed flow of the oil, and received, at the signal processor, fleet data from a database;
   detecting, via the signal processor, a feature in the ODM sensor data;
   generating, via the signal processor, an anomaly detection signal based on detecting an anomaly by comparing the feature in the ODM sensor data to a limit defined by system information stored in the fleet data;
   selecting a maintenance action request based on the anomaly detection signal;
   adjusting one or more of the feature, the anomaly, the limit, and the maintenance action request by applying, via an adaptive learning algorithm implementing processor, an adaptive learning algorithm that uses the ODM sensor data, fleet data, and feedback from field maintenance of one or more engines that evolves over time to improve an accuracy of the adaptive learning algorithm to detect the feature in the ODM sensor data; and
   applying the adaptive learning algorithm to on-board parameters to detect particles in real-time,
   wherein applying adaptive learning on ODM sensor data further comprises training a first a set of historical sensor data from fleet data to differentiate the characteristics of parameters with or without a debris particle.

2. The method of claim 1, wherein the adaptive learning algorithm is one selected from a group consisting of a machine learning algorithm, a support vector machine (SVM) algorithm, and a supervised machine learning classification algorithm.

3. The method of claim 1, further comprising:
   collecting field maintenance data to serve as ground truth of particle detection.

4. The method of claim 3, wherein field maintenance data includes one or more of data indicating whether a real particle is detected, data indicating signal noise has been falsely identified as particles, and data indicating sensor system fault, wherein as the adaptive learning algorithm continues to learn from the field maintenance data, a success rate at which the real particle is detected is increased and a false alarm rate is improved.

5. The method of claim 1, further comprising a fine-tuning procedure that includes:
   finding a discrepancy between a detection algorithm that is used to detect the features in the ODM sensor data and fleet data;
   generating additional training data from the discrepancy; and
   adding the additional training data to a training set to fine-tune the adaptive learning algorithm.

6. The method of claim 5, further comprising:
   applying the fine-tuning procedure to data from at least one selected from a group including a single engine, a collection of engines in the fleet data, and engines from a different fleet.

7. The method of claim 5, further comprising:
   applying the fine-tuning procedure to one or more selected from independently to each individual engine and a group of engines to reflect its unique characteristics.

8. The method of claim 1, wherein applying the adaptive learning algorithm continues until a detection algorithm produces detection accuracy that meets or exceeds a detection accuracy threshold.

9. The method of claim 1, further comprising:
   collecting field maintenance data from a subset of engine data obtained from a limited set stored in fleet data.

10. The method of claim 1, further comprising:
    adjusting the adaptive particle detection algorithm if additional ODM sensor parameters are included in fleet data at any time; and
    re-training adaptive particle detection algorithms.

11. The method of claim 1, further comprising:
adjusting one or more of the feature, the anomaly, the limit, and the maintenance action request upon receiving feedback from field maintenance of one or more engines.

12. The method of claim 1, further comprising:
enabling particle detection algorithms to learn from actual data from field maintenance; and
adjusting a discrepancy learned from field maintenance.

13. A system for debris particle detection with adaptive learning in a gas turbine engine, the system comprising:
a memory having computer readable instructions; and
a processor configured to execute the computer readable instructions, the computer readable instructions comprising:
receiving oil debris monitoring (ODM) sensor data from an oil debris monitor sensor installed in a mechanical system configured to flow oil through including at least one of an active flow valve and a passive flow valve, the oil debris monitor sensor configured to sense the flow of the oil;
receiving fleet data from a database;
detecting a feature in the ODM sensor data;
generating an anomaly detection signal based on detecting an anomaly by comparing the feature in the ODM sensor data to a limit defined by system information stored in the fleet data;
selecting a maintenance action based on the anomaly detection signal;
adjusting one or more of the feature, the anomaly, the limit, and the maintenance action request by applying an adaptive learning algorithm that uses the ODM sensor data, fleet data, and feedback from field maintenance of one or more engines that evolves over time to improve an accuracy of the adaptive learning algorithm to detect the feature in the ODM sensor data; and
applying the adaptive learning algorithm to on-board parameters to detect particles in real-time,
wherein applying adaptive learning on ODM sensor data further comprises training a first a set of historical sensor data from fleet data to differentiate the characteristics of parameters with or without a debris particle.

14. The system of claim 13, wherein the computer readable instructions further comprises:
collecting field maintenance data to serve as ground truth of particle detection.

15. The system of claim 13, wherein the computer readable instructions further comprises a fine-tuning procedure that includes:
finding a discrepancy between a detection algorithm that is used to detect the features in the ODM sensor data and fleet data;
generating additional training data from the discrepancy; and
adding the additional training data related to the discrepancy to a training set to fine-tune the adaptive learning algorithm.

16. A computer program product for debris particle detection with adaptive learning, the computer program product comprising a computer readable storage medium having program instructions embodied therewith, the program instructions executable by a processor to cause the processor to:
receive oil debris monitoring (ODM) sensor data from an oil debris monitor sensor and fleet data from a database;
detect, via a signal processor, a feature in the ODM sensor data;
generate, via the signal processor, an anomaly detection signal based on detecting an anomaly by comparing the feature in the ODM sensor data to a limit defined by system information stored in the fleet data;
select a maintenance action request based on the anomaly detection signal;
adjust one or more of the feature, the anomaly, the limit, and the maintenance action request by applying, via an adaptive learning algorithm implementing processor, an adaptive learning algorithm that uses the ODM sensor data, fleet data, and feedback from field maintenance of one or more engines that evolves over time to improve an accuracy of the adaptive learning algorithm to detect the feature in the ODM sensor data; and
applying the adaptive learning algorithm to on-board parameters to detect particles in real-time,
wherein applying adaptive learning on ODM sensor data further comprises training a first a set of historical sensor data from fleet data to differentiate the characteristics of parameters with or without a debris particle.

* * * * *